US012702647B2

(12) United States Patent
Sukuru et al.

(10) Patent No.: US 12,702,647 B2
(45) **Date of Patent: *Aug. 11, 2026**

(54) ENTERIC BISACODYL SOFTGEL CAPSULE

(71) Applicant: R.P. SCHERER TECHNOLOGIES, LLC, Carson City, NV (US)

(72) Inventors: Karunakar Sukuru, St. Petersburg, FL (US); Qi Fang, St. Petersburg, FL (US); Haitao Li, St. Petersburg, FL (US); Yafei Lyu, St. Petersburg, FL (US)

(73) Assignee: R.P. Scherer Technologies, LLC, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/819,296

(22) Filed: Aug. 29, 2024

(65) Prior Publication Data

US 2025/0009668 A1 Jan. 9, 2025

Related U.S. Application Data

(63) Continuation of application No. PCT/US2023/025054, filed on Jun. 12, 2023.

(60) Provisional application No. 63/351,761, filed on Jun. 13, 2022.

(51) Int. Cl.
*A61K 9/48* (2006.01)
*A61K 31/4402* (2006.01)

(52) U.S. Cl.
CPC .......... *A61K 9/4825* (2013.01); *A61K 9/4833* (2013.01); *A61K 9/4858* (2013.01); *A61K 9/4866* (2013.01); *A61K 31/4402* (2013.01)

(58) Field of Classification Search
CPC ... A61K 9/4825; A61K 9/4833; A61K 9/4866
See application file for complete search history.

(56) References Cited

U.S. PATENT DOCUMENTS

| | | | | |
|---|---|---|---|---|
| 5,656,290 | A | 8/1997 | Kelm et al. | |
| 5,670,158 | A | 9/1997 | Davis et al. | |
| 2014/0154311 | A1* | 6/2014 | Hassan | A61K 31/4402 264/153 |
| 2015/0108033 | A1* | 4/2015 | Vamvakas | A61K 9/4866 424/452 |

FOREIGN PATENT DOCUMENTS

| | | | | |
|---|---|---|---|---|
| WO | 0122942 | A1 | 4/2001 | |
| WO | 02096394 | A2 | 12/2002 | |
| WO | WO-2013155430 | A1 * | 10/2013 | A61P 37/08 |
| WO | 2020247352 | A1 | 12/2020 | |
| WO | 2021011538 | A1 | 1/2021 | |
| WO | WO-2021247518 | A1 * | 12/2021 | A61K 9/4816 |

OTHER PUBLICATIONS

International Search Report and Written Opinion for International Application No. PCT/US2023/025054, mailed Sep. 6, 2023, 23 Pages.
Non-Final Office Action for U.S. Appl. No. 18/208,635, mailed Jul. 2, 2025, 23 Pages.

* cited by examiner

*Primary Examiner* — Micah Paul Young
(74) *Attorney, Agent, or Firm* — Lowenstein Sandler LLP

(57) ABSTRACT

Softgel capsules comprise a fill material and a shell composition, wherein the fill composition includes bisacodyl and the shell composition includes a film forming material and an enteric polymer. The softgel capsules further include 5 parts by weight of bisacodyl based on 100 parts by weight of the fill material. A method for producing the softgel capsule using a gel conversion is also provided.

22 Claims, No Drawings

ENTERIC BISACODYL SOFTGEL CAPSULE

CROSS REFERENCE TO RELATED APPLICATION(S)

The present application claims priority to U.S. Provisional Patent Application No. 63/351,761 filed on Jun. 13, 2022, the entire contents of which are incorporated in its entirety.

FIELD OF THE INVENTION

The present invention relates to an enteric softgel capsule, wherein the softgel capsule includes a shell composition and a fill composition. Specifically, the enteric softgel capsule includes bisacodyl in the fill composition. Methods of preparation of such dosage forms and methods of use thereof are also disclosed.

BACKGROUND OF THE INVENTION

Capsule dosage forms are commonly used for oral administration of a variety of pharmaceuticals. The capsules can be, for example, soft gelatin shell or hard shell (animal or vegetable variety). Softgel capsules provide numerous advantages including fast dissolution, taste-masking, ease of swallowing, fewer excipients as compared to tablets, delivery of a liquid matrix that solubilizes and improves oral bioavailability of a marginally hydrophilic compound, delivery of low and ultra-low doses of a compound, delivery of low melting temperature compounds and minimization of dust generation during manufacturing and thus, improved safety for production personnel.

Soft capsules, in particular, soft gelatin capsules (or softgel capsules), provide a dosage form which is more readily accepted by patients, since the capsules are easy to swallow and need not be flavored in order to mask any unpleasant taste of the active agent. Softgel encapsulation of drugs further provides the potential to improve the bioavailability of the pharmaceutical agents. For example, active ingredients may be rapidly released in liquid form as soon as the gelatin shell ruptures.

SUMMARY OF THE INVENTION

In some embodiments, a softgel capsule includes a fill material and a shell composition, wherein the fill material comprises bisacodyl or a pharmaceutically acceptable salt thereof and wherein the shell composition comprises a film forming material and an enteric polymer.

In some embodiments, the film forming material comprises an animal derived polymer or a non-animal derived polymer. In certain embodiments, the animal derived polymer comprises gelatin. In other embodiments, the non-animal derived polymer comprises pectin.

In some embodiments, the shell composition further comprises dextrose. In some embodiments, the shell composition further comprises a plasticizer.

In some embodiments, the enteric polymer is pectin. In certain embodiments, the pectin is an amidated pectin, a non-amidated pectin or combinations thereof. In some embodiments, the shell composition comprises from about 2 wt % to about 20 wt % of pectin. In some embodiments, the shell composition comprises non-amidated pectin.

In some embodiments, the shell composition of the softgel capsule comprises about 30 wt % to about 80 wt % of a gelatin. In some embodiments, the shell composition of the softgel capsule comprises about 2 wt % to about 20 wt % of pectin. In some embodiments, the shell composition of the softgel capsule comprises about 0.01 wt % to about 4 wt % of dextrose. In some embodiments, the shell composition comprises about 2 wt % to about 40 wt % of a plasticizer.

In certain embodiments, the film forming material includes gelatin, wherein the gelatin comprises Type A gelatin, Type B gelatin and mixtures thereof. In some embodiments, the gelatin comprises fish gelatin, hide gelatin, bone gelatin and mixtures thereof.

In some embodiments, the shell composition further includes a plasticizer, wherein the plasticizer comprises glycerol, glycerin, sorbitol, and sorbitol and sorbitan solution and combinations thereof.

In some embodiments, the shell composition of the softgel capsule further comprises water. In some embodiments, the shell composition comprises from about 8 wt % to about 20 wt % of water.

In some embodiments, the shell composition of the softgel capsule further comprises a gelling agent. In some embodiments, the shell composition comprises from about 0.1 wt % to about 2 wt % of the gelling agent. In certain embodiments, the gelling agent is a gellan gum.

In some embodiments, the fill material further comprises an antioxidant. In certain embodiments, the fill material further comprises butylated hydroxytoluene (BHT). In certain embodiments, the fill material further comprises butylated hydroxyanisole (BHA). In some embodiments, the fill material comprises about 0.001 parts by weight to about 2 parts by weight of antioxidant based on 100 parts by weight of the fill material. In some embodiments, the fill material comprises about 0.001 parts by weight to about 0.5 parts by weight of BHT based on 100 parts by weight of the fill material. In some embodiments, the fill material comprises about 0.1 parts by weight to about 2 parts by weight of BHA based on a 100 parts by weight of the fill material.

In some embodiments, the fill material further comprises a lipid. In some embodiments, the lipid is soybean oil. In some embodiments, the fill material comprises from about 90 wt % to about 95 wt % of lipid based on a total composition of the fill material. In some embodiments, the fill material may further include a suspending agent, wherein the suspending agent is hydrogenated vegetable oil.

In some embodiments, the fill material comprises about 5 parts by weight to about 10 parts by weight of bisacodyl based on 100 parts by weight of the fill material.

In some embodiments, the shell composition further comprises a methacrylic copolymer.

In some embodiments, the softgel capsule may disintegrate in pH 6.8 buffer in about 60 minutes or less, in about 45 minutes or less, in about 30 minutes or less, in about 20 minutes or less, in about 10 minutes or less, or in about 5 minutes or less when tested at 25° C./60% RH at 1 month, 2 months, 3 months, 6 months, 12 months, or 24 months.

In some embodiments, the softgel capsule may remain intact for at least about 15 minutes, at least about 30 minutes, at least about 1 hour, at least about 2 hours, at least about 3 hours, at least about 4 hours, or at least about 5 hours in pH 1.2 medium and may disintegrate in pH 6.8 buffer in about 60 minutes or less, in about 45 minutes or less, in about 30 minutes or less, in about 20 minutes or less, in about 10 minutes or less, or in about 5 minutes or less when tested at 25° C./60% RH at 1 month, 2 months, 3 months, 6 months, 12 months, or 24 months.

In some embodiments, the softgel capsule may disintegrate in pH 6.8 buffer in about 60 minutes or less, in about 45 minutes or less, in about 30 minutes or less, in about 20 minutes or less, in about 10 minutes or less, or in about 5 minutes or less when tested at 30° C./65% RH at 1 month, 2 months, 3 months, 6 months, 12 months, or 24 months.

In some embodiments, the softgel capsule may remain intact for at least about 15 minutes, at least about 30 minutes, at least about 1 hour, at least about 2 hours, at least about 3 hours, at least about 4 hours, or at least about 5 hours in pH 1.2 medium and may disintegrate in pH 6.8 buffer in about 60 minutes or less, in about 45 minutes or less, in about 30 minutes or less, in about 20 minutes or less, in about 10 minutes or less, or in about 5 minutes or less when tested at 30° C./65% RH at 1 month, 2 months, 3 months, 6 months, 12 months, or 24 months.

In some embodiments, the softgel capsule may disintegrate in pH 6.8 buffer in about 60 minutes or less, in about 45 minutes or less, in about 30 minutes or less, in about 20 minutes or less, in about 10 minutes or less, or in about 5 minutes or less when tested at 49° C./75% RH at 1 month, 2 months, 3 months, 6 months, 12 months, or 24 months.

In some embodiments, the softgel capsule may remain intact for at least about 15 minutes, at least about 30 minutes, at least about 1 hour, at least about 2 hours, at least about 3 hours, at least about 4 hours, or at least about 5 hours in pH 1.2 medium and may disintegrate in pH 6.8 buffer in about 60 minutes or less, in about 45 minutes or less, in about 30 minutes or less, in about 20 minutes or less, in about 10 minutes or less, or in about 5 minutes or less when tested at 40° C./75% RH at 1 month, 2 months, 3 months, 6 months, 12 months, or 24 months.

In some embodiments, the softgel capsule may have an assay stability of at least about 90% when tested at 25° C./60% RH at 1 month, 2 months, 3 months, 6 months, 12 months, or 24 months.

In some embodiments, the softgel capsule may have an assay stability of at least about 92% when tested at 25° C./60% RH at 1 month, 2 months, 3 months, 6 months, 12 months, or 24 months.

In some embodiments, the softgel capsule may have an assay stability of at least about 94% when tested at 25° C./60% RH at 1 month, 2 months, 3 months, 6 months, 12 months, or 24 months.

In some embodiments, the softgel capsule may have an assay stability of at least about 96% when tested at 25° C./60% RH at 1 month, 2 months, 3 months, 6 months, 12 months, or 24 months.

In some embodiments, the softgel capsule may have an assay stability of at least about 98% when tested at 25° C./60% RH at 1 month, 2 months, 3 months, 6 months, 12 months, or 24 months.

In some embodiments, the softgel capsule may have an assay stability of at least about 99% when tested at 25° C./60% RH at 1 month, 2 months, 3 months, 6 months, 12 months, or 24 months.

In some embodiments, the softgel capsule may have an assay stability of at least about 90% when tested at 30° C./65% RH at 1 month, 2 months, 3 months, 6 months, 12 months, or 24 months.

In some embodiments, the softgel capsule may have an assay stability of at least about 92% when tested at 30° C./65% RH at 1 month, 2 months, 3 months, 6 months, 12 months, or 24 months.

In some embodiments, the softgel capsule may have an assay stability of at least about 94% when tested at 30° C./65% RH at 1 month, 2 months, 3 months, 6 months, 12 months, or 24 months.

In some embodiments, the softgel capsule may have an assay stability of at least about 96% when tested at 30° C./65% RH at 1 month, 2 months, 3 months, 6 months, 12 months, or 24 months.

In some embodiments, the softgel capsule may have an assay stability of at least about 98% when tested at 30° C./65% RH at 1 month, 2 months, 3 months, 6 months, 12 months, or 24 months.

In some embodiments, the softgel capsule may have an assay stability of at least about 99% when tested at 30° C./65% RH at 1 month, 2 months, 3 months, 6 months, 12 months, or 24 months.

In some embodiments, the softgel capsule may have an assay stability of at least about 90% when tested at 40° C./75% RH at 1 month, 2 months, 3 months, 6 months, 12 months, or 24 months.

In some embodiments, the softgel capsule may have an assay stability of at least about 92% when tested at 40° C./75% RH at 1 month, 2 months, 3 months, 6 months, 12 months, or 24 months.

In some embodiments, the softgel capsule may have an assay stability of at least about 94% when tested at 40° C./75% RH at 1 month, 2 months, 3 months, 6 months, 12 months, or 24 months.

In some embodiments, the softgel capsule may have an assay stability of at least about 96% when tested at 40° C./75% RH at 1 month, 2 months, 3 months, 6 months, 12 months, or 24 months.

In some embodiments, the softgel capsule may have an assay stability of at least about 98% when tested at 40° C./75% RH at 1 month, 2 months, 3 months, 6 months, 12 months, or 24 months.

In some embodiments, the softgel capsule may have an assay stability of at least about 99% when tested at 40° C./75% RH at 1 month, 2 months, 3 months, 6 months, 12 months, or 24 months.

In some embodiments, the softgel capsule may remain intact for at least about 15 minutes, at least about 30 minutes, at least about 1 hour, at least about 2 hours, at least about 3 hours, at least about 4 hours, or at least about 5 hours in an acidic medium, wherein a dissolution test is performed in a USP Apparatus II with paddles at a speed of 50 rpm in pH 1.2 medium.

In some embodiments, the softgel capsule may remain intact for at least about 15 minutes, at least about 30 minutes, at least about 1 hour, at least about 2 hours, at least about 3 hours, at least about 4 hours, or at least about 5 hours, wherein a disintegration test is performed in a USP Apparatus II with paddles at a speed of 50 rpm in pH 1.2 medium.

In some embodiments, the softgel capsule may disintegrate in pH 6.8 buffer in about 60 minutes or less, in about 45 minutes or less, in about 30 minutes or less, in about 20 minutes or less, in about 10 minutes or less, or in about 5 minutes or less.

In some embodiments, the softgel capsule may remain intact for at least about 15 minutes, at least about 30 minutes, at least about 1 hour, at least about 2 hours, at least about 3 hours, at least about 4 hours, or at least about 5 hours in pH 1.2 medium and may disintegrate in pH 6.8 buffer in about 60 minutes or less, in about 45 minutes or less, in about 30 minutes or less, in about 20 minutes or less, in about 10 minutes or less, or in about 5 minutes or less.

In some embodiments, the total impurity does not exceed about 0.5%, about 0.4%, about 0.3%, about 0.2%, about 0.1% or about 0.01%, wherein the total impurity is measured per current USP Monograph test method.

In some embodiments, the total impurity does not exceed about 0.3%.

In another embodiment, a process for producing a softgel capsule including a fill material and a shell composition, wherein the fill material includes bisacodyl and the shell composition includes a film forming material and an enteric polymer includes encapsulating the fill composition in the shell composition to form the softgel capsule and drying the softgel capsule. In another embodiment, the process further comprises, prior to encapsulating, a gel conversion occurs for the shell composition.

DETAILED DESCRIPTION OF THE INVENTION

The present invention advances the state of the art by developing delayed release oral dosage forms, in particular, delayed release softgel capsules, that include an enteric polymer. The delayed release softgel capsules of the present invention do not dissolve in a gastric environment of the stomach, but rather dissolve in the intestines. Such mechanism is beneficial for delivery of active ingredients that may cause stomach irritation or are sensitive to the acidic environment of the stomach.

As used herein, "pharmaceutically active ingredient" refers to a drug or compound that may be used in the diagnosis, cure, mitigation, treatment, or prevention of a condition. The term "condition" or "conditions" refers to those medical conditions that can be treated or prevented by administration to a subject of an effective amount of an active agent.

As used herein, the term "active ingredient" refers to any material that is intended to produce a therapeutic, prophylactic, or other intended effect, whether or not approved by a government agency for that purpose. This term with respect to a specific agent includes the pharmaceutically active agent, and all pharmaceutically acceptable salts, solvates and crystalline forms thereof, where the salts, solvates and crystalline forms are pharmaceutically active.

As used herein, the terms "therapeutically effective" and an "effective amount" refer to the amount of active agent or the rate at which it is administered which is needed to produce a desired therapeutic result.

As used herein, "shell" or "shell composition" refers to the shell of a softgel capsule which encapsulates a fill material.

All references to wt % throughout the specifications and the claims refer to the weight of the component in reference to the weight of the entire composition and may also be designated as w/w.

As used herein, "fill material" or "fill" refers to the composition that is encapsulated by the capsule shell and contains at least one pharmaceutically active ingredient.

As used herein, "about" refers to any values that are within a variation of ±10%, such that "about 10" would include from 9 to 11. As used herein, "a," "an," or "the" refers to one or more, unless otherwise specified. Thus, for example, reference to "an excipient" includes a single excipient as well as a mixture of two or more different excipients, and the like.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

In some embodiments, the active pharmaceutical ingredient may be bisacodyl or salts thereof.

According to an embodiment, a softgel capsule may include a fill material and a shell composition, wherein the fill material may include bisacodyl or a pharmaceutical acceptable salt thereof, wherein the shell composition includes a film forming material and an enteric polymer. In some embodiments, the enteric polymer may be an amidated, non-amidated or a combination thereof.

In some embodiments, the fill material may include bisacodyl or a pharmaceutical acceptable salt thereof and a lipid. In other embodiments, the fill material may include additional fill components such as a suspending agent, flavoring agents, sweetening agents, coloring agents and fillers, an antioxidant or other pharmaceutically acceptable excipients or additives such as synthetic dyes and mineral oxides. In some embodiments, the suspending agent may be a hydrogenated vegetable oil.

In some embodiments, the lipids in the dosage form may be selected, without limitations, from the group consisting of almond oil, argan oil, avocado oil, borage seed oil, canola oil, cashew oil, castor oil, hydrogenated castor oil, cocoa butter, coconut oil, colza oil, corn oil, cottonseed oil, grape seed oil, hazelnut oil, hemp oil, hydroxylated lecithin, lecithin, linseed oil, macadamia oil, mango butter, manila oil, mongongo nut oil, olive oil, palm kernel oil, palm oil, peanut oil, pecan oil, perilla oil, pine nut oil, pistachio oil, poppy seed oil, pumpkin seed oil, rice bran oil, safflower oil, sesame oil, shea butter, soybean oil, sunflower oil, hydrogenated vegetable oil, walnut oil, and watermelon seed oil. Other oil and fats may include, but not be limited to, fish oil (omega-3), krill oil, animal or vegetable fats, e.g., in their hydrogenated form, fractionated coconut oil, medium chain triglycerides, free fatty acids and mono-, di-, and tri-glycerides with C8-, C10-, C12-, C14-, C16-, C18-, C20- and C22-fatty acids, and combinations thereof.

In some embodiments, the antioxidant may be butylated hydroxytoluene (BHT), butylated hydroxyanisole (BHA), or a combination thereof.

In some embodiments, the fill material may include about 1 mg per capsule to about 25 mg per capsule, or about 2 mg per capsule to about 20 mg per capsule of bisacodyl, or about 5 mg per capsule to about 15 mg per capsule, or about 5 mg per capsule to about 10 mg per capsule, or about 7.5 mg per capsule to about 10 mg per capsule of bisacodyl. In one embodiment, the bisacodyl may be included in an amount of about 5 parts by weight to about 10 parts by weight based on 100 parts by weight of the fill material.

In some embodiments, the lipid may be included in an amount from about 85 parts by weight, about 90 parts by weight or about 95 parts by weight based on 100 parts by weight based on the fill material.

In some embodiments, an antioxidant may be included in the fill material. The antioxidant may be included in an amount of about 0.001 parts by weight to about 2 parts by weight based on 100 parts by weight based on the fill material.

In an embodiment, the gelatin in the shell composition may include Type A gelatin, Type B gelatin, a hide or skin gelatin and/or a bone gelatin used alone or in combination. In one embodiment, the gelatin may be a pigskin gelatin or a Type B gelatin. In another embodiment, there may be only one type of gelatin. In yet another embodiment, the gelatin may be a combination of at least two types of gelatins. In an embodiment, the amount of gelatin in the shell composition may be about 20 wt % to about 80 wt %, or from about 30 wt % to about 60 wt %, or from about 35 wt % to about 55 wt %.

In one embodiment, the shell composition includes dextrose. In an embodiment, the amount of dextrose in the shell composition is about 0.005 wt % to about 5 wt %, or about 0.01 wt % to about 4 wt %, or from about 0.1 wt % to about 3.5 wt %, or about 0.15 wt % to about 3 wt %, or from about 0.15 wt % to about 2.5 wt % or about 0.2 wt % to about 2 wt %, or from about 0.1 wt % to about 1.5 wt %, or from about 0.2 wt % to about 1 wt %. The dextrose may be added to the capsule shell to mitigate potential reduction in gel strength. The concentration of dextrose in the shell composition may be in an effective amount to improve the gel strength but not so high that it would interfere with the seal.

In some embodiments, the shell composition may include pectin. In some embodiments, the pectin may be a low methoxy pectin. In some embodiments, the pectin may be an amidated pectin, non-amidated pectin or a combination thereof. In an embodiment, the pectin is low methylester (LM) pectin with Degree of Esterification lower than 50. In some embodiments, the pectin is LMS-318, SPL-12, LM-102 AS-Z and/or LM-12 CG-Z. In other embodiments, the low methoxy (LM) pectin may be LM Pectin (P-25), LM Pectin (445C), LM Pectin (100C) or a combination thereof. Too much pectin in the dosage form may reduce the gel strength of the softgel capsule which may in turn adversely affect the scalability of the softgel capsule. Therefore, pectin may be added to the dosage form at a concentration that is sufficiently high to form a delayed release dosage form and at the same time is sufficiently low to mitigate the reduction in gel strength. In an embodiment, an amount of pectin in the shell composition is about 2 wt % to about 20 wt %, from about 3 wt % to about 15 wt %, from about 2 wt % to about 12 wt %, from about 3 wt % to about 5.5 wt %, and from about 5 wt % to about 10 wt %.

In an embodiment, the shell composition may also include a plasticizer. In some embodiments, the plasticizer in the shell composition may include glycerol, glycerin, sorbitol, and sorbitol and sorbitan solution and combinations thereof. Other suitable plasticizers may include, but not be limited to, sugar alcohol plasticizer such as isomalt, maltitol, xylitol, erythritol, adonitol, dulcitol, pentaerythritol, or mannitol; or polyol plasticizer such as diglycerin, dipropylene glycol, polyethylene glycol up to 10,000 MW, neopentyl glycol, propylene glycol, 1,3-propanediol, 2-methyl-1,3-propanediol, trimethylolpropane, polyether polyol, ethanol amines; and mixtures thereof. Other exemplary plasticizers may also include, without limitations, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, citrate ester-type plasticizers, and triacetin. Such plasticizers may include 1,2-butylene glycol, 2,3-butylene glycol, styrene glycol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, glyceryl monostearate, polysorbate 80, acetyl triethyl citrate, tributyl citrate and allyl glycolate, and mixtures thereof.

In an embodiment, the amount of plasticizer in the shell composition is about 2 wt % to about 40 wt %, or from about 5 wt % to about 35 wt %, or from about 10 wt % to about 30 wt %, or from about 15 wt % to about 25 wt %.

In an embodiment, the shell composition may also include a gelling agent. In some embodiments, the gelling agent may be a gellan gum, agar, alginate, guar gum or Locus bean gum. For example, the gellan gum may be a Kelcogel CG-LA gellan gum.

The shell composition may also include water. In some embodiments, water may be included in the shell composition in an amount of 5 wt % to about 60 wt %, 10 wt % to about 50 wt %, or from about 20 wt % to about 40 wt %, or about 5 wt % to about 25 wt %, or about 8 wt % to about 20 wt %, or about 30 wt % to about 45 wt % based on the total shell composition.

In an embodiment, the shell composition may optionally comprise additional agents such as coloring agents, flavoring agents, sweetening agents, fillers, antioxidants, diluents, pH modifiers or other pharmaceutically acceptable excipients or additives such as synthetic dyes and mineral oxides.

Exemplary suitable coloring agents may include, but not be limited to, colors such as e.g., white, black, yellow, blue, green, pink, red, orange, violet, indigo, and brown. In specific embodiments, the color of the dosage form can indicate the contents (e.g., one or more active ingredients) contained therein.

Exemplary suitable flavoring agents may include, but not be limited to, "flavor extract" obtained by extracting a part of a raw material, e.g., animal or plant material, often by using a solvent such as ethanol or water; natural essences obtained by extracting essential oils from the blossoms, fruit, roots, etc., or from the whole plants.

Additional exemplary flavoring agents that may be in the dosage form may include, but not be limited to, breath freshening compounds like menthol, spearmint, and cinnamon, coffee beans, other flavors or fragrances such as fruit flavors (e.g., cherry, orange, grape, etc.), especially those used for oral hygiene, as well as actives used in dental and oral cleansing such as quaternary ammonium bases. The effect of flavors may be enhanced using flavor enhancers like tartaric acid, citric acid, vanillin, or the like.

Exemplary sweetening agents may include, but not be limited to, one or more artificial sweeteners, one or more natural sweeteners, or a combination thereof. Artificial sweeteners include, e.g., acesulfame and its various salts such as the potassium salt (available as Sunett®), alitame, aspartame (available as NutraSweet® and Equal®), salt of aspartame-acesulfame (available as Twinsweet®), neohesperidin dihydrochalcone, naringin dihydrochalcone, dihydrochalcone compounds, neotame, sodium cyclamate, saccharin and its various salts such as the sodium salt (available as Sweet'N Low®), stevia, chloro derivatives of sucrose such as sucralose (available as Kaltame® and Splenda®), and mogrosides. Natural sweeteners include, e.g., glucose, dextrose, invert sugar, fructose, sucrose, glycyrrhizin; monoammonium glycyrrhizinate (sold under the trade name MagnaSweet®); Stevia rebaudiana (Stevioside), natural intensive sweeteners, such as Lo Han Kuo, polyols such as sorbitol, and sorbitol and sorbitan, mannitol, xylitol, erythritol, and the like.

In some embodiments, a methacrylic copolymer may be included in the shell composition. In an embodiment, the shell composition may include a methacrylic copolymer in an amount of about 0.1 wt % to about 5 wt %, or from about 1 wt % to about 4 wt %, or from about 2 wt % to about 3 wt % based on the total weight of the shell composition. In some embodiments, the methacrylic copolymer may be Kollicoat MAE 100P. Without being limited to a theory, the inventors believe that the methacrylic copolymer enhances the enteric property of the shell composition.

In some embodiments, the shell composition and/or the softgel capsule may be tested in a dissolution test performed in a USP Apparatus II with paddles at a speed of 50 rpm in pH 1.2 medium or simulated gastric fluid. The softgel capsule according to this embodiment may remain intact for at least about 15 minutes, at least about 30 minutes, at least about one hour, at least about two hours, at least about three hours, at least about four hours, or at least about five hours, in acidic medium and may disintegrate in pH 6.8 buffer or simulated intestinal fluid in about 30 minutes or less, in about 20 minutes or less, in about 10 minutes or less, or in about 5 minutes or less.

In some embodiments, the shell composition and/or the softgel capsule may be tested in a disintegration test performed in a USP/EP Disintegration Apparatus in pH 1.2 medium or simulated gastric fluid. The softgel capsule according to this embodiment may remain intact for at least about 15 minutes, at least about 30 minutes, at least about one hour, at least about two hours, at least about three hours, at least about four hours, or at least about five hours, in acidic medium and may disintegrate in pH 6.8 buffer or simulated intestinal fluid in about 30 minutes or less, in about 20 minutes or less, in about 10 minutes or less, or in about 5 minutes or less.

In some embodiments, the shell composition and/or the softgel capsule may be tested in a two stage dissolution test performed in a USP Apparatus II with paddles at a speed of 50 rpm in 750 ml pH 1.2 0.1 N HCl medium or simulated gastric fluid maintained at 37° C. The softgel capsule according to this embodiment may remain intact for at least about 15 minutes, at least about 30 minutes, at least about one hour, at least about two hours, at least about three hours, at least about four hours, or at least about five hours, in acidic medium and may disintegrate in 1000 ml pH 6.8 buffer or simulated intestinal fluid in about 60 minutes or less, 45 minutes or less, 30 minutes or less, in about 20 minutes or less, in about 10 minutes or less, or in about 5 minutes or less.

In some embodiments, the shell composition and/or the softgel capsule may be tested in a two stage disintegration test performed in a USP/EP Disintegration Apparatus in pH 1.2 0.1 N HCl medium or simulated gastric fluid maintained at 37° C. The softgel capsule according to this embodiment may remain intact for at least about 15 minutes, at least about 30 minutes, at least about one hour, at least about two hours, at least about three hours, at least about four hours, or at least about five hours, in acidic medium and may disintegrate in pH 6.8 buffer or simulated intestinal fluid in about 60 minutes or less, 45 minutes or less, 30 minutes or less, in about 20 minutes or less, in about 10 minutes or less, or in about 5 minutes or less.

In some embodiments, the disintegration test may be performed for about 150 minutes, about 120 minutes, about 105 minutes, about 90 minutes, about 75 minutes, about 60 minutes, about 45 minutes, about 30 minutes, about 15 minutes, about 10 minutes, or about 5 minutes.

In some embodiments, the softgel capsule may have an assay stability of at least about 80%, at least 85%, at least 90%, at least about 91%, at least about 92%, at least about 93%, at least about 94%, at least about 95%, at least 96%, at least 97%, at least about 98% or at least 99% when tested at 25° C./60% RH at 1 month, 2 months, 3 months, 6 months, 12 months, or 24 months. In some embodiments, the softgel capsule may have an assay stability of at least about 80%, at least 85%, at least 90%, at least about 91%, at least about 92%, at least about 93%, at least about 94%, at least about 95%, at least 96%, at least 97%, at least about 98% or at least 99% when tested at 30° C./65% RH at 1 month, 2 months, 3 months, 6 months or 12 months. In some embodiments, the softgel capsule may have an assay stability of at least about 80%, at least 85%, at least 90%, at least about 91%, at least about 92%, at least about 93%, at least about 94%, at least about 95%, at least 96%, at least 97%, at least about 98% or at least 99% when tested at 40° C./75% RH at 1 month, 2 months, 3 months, 6 months or 12 months. As used herein, the assay stability is measured as the amount of bisacodyl remaining after an accelerated time period stored at a specified temperature and relative humidity.

The amount of impurity may also be measured and analyzed, e.g., after an accelerated time period of about 1 month, about 2 months, about 3 months, about 6 months or about 12 months. In some embodiments, the softgel capsule may have less than about 2.0%, or less than about 1.75%, or less than about 1.5%, or less than about 1.25%, or less than about 1%, or less than about 0.75%, or less than about 0.5%, or less than about 0.25%, or 0% of total impurities. In certain embodiments, the softgel capsules may have less than about 0.1%, less than about 0.075%, less than about 0.05%, less than about 0.025%, or 0% of impurity RRT 0.822. In certain embodiments, the softgel capsule may have less than about 0.1%, or less than about 0.075%, or less than about 0.05%, or less than about 0.025% or 0% of impurity RRT 0.935.

Encapsulation of the fill material can be accomplished in any conventional manner. As an example, a rotary die encapsulation machine may be used. In some embodiments, gel conversion may be used to color the gel mass to encapsulate the fill composition. In some embodiments, the gel conversion includes the shell composition, an opacifier and a colorant. The opacifier may be titanium dioxide. The opacifiers may also be iron oxides. The colorant may include FD&C Yellow #6. The gel conversion may also include water and plasticizer. In some embodiments, the colorant may be included in an amount of about 0.5 g to about 2.5 g per kilogram of the shell composition. In some embodiments, the opacifier may be included in an amount of about 2 g to about 5 g per kilogram of the shell composition. In other embodiments, water may be included in an amount of about 40 grams to about 60 grams per kilogram of the shell composition.

According to an embodiment, the softgel capsule is prepared by (a) preparing the fill composition, the fill composition including a pharmaceutically active ingredient; and (b) encapsulating the fill composition in a shell composition. The encapsulation process may also include a sub-step of preparing the shell composition by, for example, admixing a gelatin, dextrose, a pectin a plasticizer and optionally a gum or synthetic polymer. The shell composition may further undergo a gel conversion before encapsulation.

LIST OF ITEMS

1. A softgel capsule comprising:
   (a) a fill material; and
   (b) a shell composition,
   wherein the fill material comprises bisacodyl or a pharmaceutically acceptable salt and wherein the shell composition comprises a film forming material and an enteric polymer.

2. The softgel capsule of item 1, wherein the film forming material comprises an animal derived polymer or a non-animal derived polymer.

3. The softgel capsule of item 2, wherein the animal derived polymer comprises gelatin.

4. The softgel capsule of item 2, wherein non-animal derived polymer comprises gellan gum.

5. The softgel capsule of any one of the preceding items, wherein the shell composition further comprises dextrose.

6. The softgel capsule of any one of the preceding items, wherein the shell composition further comprises a plasticizer.

7. The softgel capsule of any one of the preceding items, wherein the enteric polymer is pectin.

8. The softgel capsule of any one of items 1-6, wherein the enteric polymer is methyl acrylic acid copolymer.

9. The softgel capsule of item 7, wherein the pectin is an amidated pectin or a non-amidated pectin or combinations thereof.

10. The softgel capsule of item 3, wherein the shell composition comprises about 30 wt % to about 80 wt % of a gelatin.

11. The softgel capsule of item 7, wherein the shell composition comprises about 2 wt % to about 20 wt % of pectin.

12. The softgel capsule of item 8, wherein the shell composition comprises about 2 wt % to about 16 wt % of methyl acrylic acid copolymer.

13. The softgel capsule of item 5, wherein the shell composition comprises about 0.01 wt % to about 4 wt % of dextrose.

14. The softgel capsule of item 6, wherein the shell composition comprises about 2 wt % to about 40 wt % of a plasticizer.

15. The softgel capsule of item 3, wherein the gelatin comprises Type A gelatin, Type B gelatin and mixtures thereof.

16. The softgel capsule of item 3, wherein the gelatin comprises fish gelatin, hide gelatin, bone gelatin and mixtures thereof.

17. The softgel capsule of item 6, wherein the plasticizer comprises glycerol, glycerin, sorbitol, sorbitol and sorbitan solution and combinations thereof.

18. The softgel capsule of any one of items 1-17, wherein the shell composition further comprises water.

19. The softgel capsule of item 18, wherein the shell composition comprises from about 8 wt % to about 20 wt % of water.

20. The softgel capsule of any one of items 1-19, wherein the shell composition further comprises a gelling agent.

21. The softgel capsule of item 7, wherein the shell composition comprises from about 2 wt % to about 12 wt % of pectin.

22. The softgel capsule of item 20, wherein the shell composition comprises from about 0.1 wt % to about 2 wt % of the gelling agent.

23. The softgel capsule of item 18 or 22, wherein the gelling agent is a gellan gum.

24. The softgel capsule of any of the preceding items, wherein the fill material further comprises an antioxidant.

25. The softgel capsule of item 24, wherein the fill material further comprises butylated hydroxytoluene (BHT).

26. The softgel capsule of items 24 or 25, wherein the fill material further comprises butylated hydroxyanisole (BHA).

27. The softgel capsule of any one items 1-26, wherein the fill material further comprises a lipid.

28. The softgel capsule of item 27, wherein the lipid is soybean oil.

29 The softgel capsule of any one items 1-28, wherein the fill material further comprises a suspending agent.

30 The softgel capsule of item 29, wherein the suspending agent is hydrogenated vegetable oil.

31. The softgel capsule of item 27, wherein the fill material comprises from about 90 wt % to about 95 wt % of lipid based on a total composition of the fill material.

32. The softgel capsule of any of the preceding items, wherein the fill material comprises about 5 parts by weight to about 10 parts by weight of bisacodyl based on 100 parts by weight of the fill material.

33. The softgel capsule of item 24, wherein the fill material comprises about 0.001 parts by weight to about 2 parts by weight of antioxidant based on 100 parts by weight of the fill material.

34. The softgel capsule of item 25, wherein the fill material comprises about 0.001 parts by weight to about 0.5 parts by weight of BHT based on 100 parts by weight of the fill material.

35. The softgel capsule of item 26, wherein the fill material comprises about 0.1 parts by weight to about 2 parts by weight of BHA based on a 100 parts by weight of the fill material.

36. The softgel capsule of item 9, wherein the shell composition comprises non-amidated pectin.

37. The softgel capsule of any one of the preceding items, wherein the softgel capsule disintegrates in pH 6.8 buffer in about 60 minutes or less, in about 45 minutes or less, in about 30 minutes or less, in about 20 minutes or less, in about 10 minutes or less, or in about 5 minutes or less when tested at 25° C./60% RH at 1 month, 2 months, 3 months, 6 months, 12 months, or 24 months.

38. The softgel capsule of any one of the preceding items, wherein the softgel capsule remains intact for at least about 15 minutes, at least about 30 minutes, at least about 1 hour, at least about 2 hours, at least about 3 hours, at least about 4 hours, or at least about 5 hours in pH 1.2 medium and disintegrates in pH 6.8 buffer in about 60 minutes or less, in about 45 minutes or less, in about 30 minutes or less, in about 20 minutes or less, in about 10 minutes or less, or in about 5 minutes or less when tested at 25° C./60% RH at 1 month, 2 months, 3 months, 6 months, 12 months, or 24 months.

39. The softgel capsule of any one of the preceding items, wherein the softgel capsule disintegrates in pH 6.8 buffer in about 60 minutes or less, in about 45 minutes or less, in about 30 minutes or less, in about 20 minutes or less, in about 10 minutes or less, or in about 5 minutes or less when tested at 30° C./65% RH at 1 month, 2 months, 3 months, 6 months, 12 months, or 24 months.

40. The softgel capsule of any one of the preceding items, wherein the softgel capsule remains intact for at least about 15 minutes, at least about 30 minutes, at least about 1 hour, at least about 2 hours, at least about 3 hours, at least about 4 hours, or at least about 5 hours in pH 1.2 medium and disintegrates in pH 6.8 buffer in about 60 minutes or less, in about 45 minutes or less, in about 30 minutes or less, in about 20 minutes or less, in about 10 minutes or less, or in about 5 minutes or less when tested at 30° C./65% RH at 1 month, 2 months, 3 months, 6 months, 12 months, or 24 months.

41. The softgel capsule of any one of the preceding items, wherein the softgel capsule disintegrates in pH 6.8 buffer in about 60 minutes or less, in about 45 minutes or less, in about 30 minutes or less, in about 20 minutes or less, in about 10 minutes or less, or in about 5 minutes or less when tested at 49° C./75% RH at 1 month, 2 months, 3 months, 6 months, 12 months, or 24 months.

42. The softgel capsule of any one of the preceding items, wherein the softgel capsule remains intact for at least about 15 minutes, at least about 30 minutes, at least about 1 hour, at least about 2 hours, at least about 3 hours, at least about 4 hours, or at least about 5 hours in pH 1.2 medium and disintegrates in pH 6.8 buffer in about 60 minutes or less, in about 45 minutes or less, in about 30 minutes or less, in about 20 minutes or less, in about 10 minutes or less, or in about 5 minutes or less when tested at 40° C./75% RH at 1 month, 2 months, 3 months, 6 months, 12 months, or 24 months.

43. The softgel capsule of any one of items 37-42, wherein the enteric polymer is amidated pectin.

44. The softgel capsule of any one of the preceding items, wherein the softgel capsule has an assay stability of at least about 90% when tested at 25° C./60% RH at 1 month, 2 months, 3 months, 6 months, 12 months, or 24 months.

45. The softgel capsule of any one of the preceding items, wherein the softgel capsule has an assay stability of at least about 92% when tested at 25° C./60% RH at 1 month, 2 months, 3 months, 6 months, 12 months, or 24 months.

46. The softgel capsule of any one of the preceding items, wherein the softgel capsule has an assay stability of at least about 94% when tested at 25° C./60% RH at 1 month, 2 months, 3 months, 6 months, 12 months, or 24 months.

47. The softgel capsule of any one of the preceding items, wherein the softgel capsule has an assay stability of at least about 96% when tested at 25° C./60% RH at 1 month, 2 months, 3 months, 6 months, 12 months, or 24 months.

48. The softgel capsule of any one of the preceding items, wherein the softgel capsule has an assay stability of at least about 98% when tested at 25° C./60% RH at 1 month, 2 months, 3 months, 6 months, 12 months, or 24 months.

49. The softgel capsule of any one of the preceding items, wherein the softgel capsule has an assay stability of at least about 99% when tested at 25° C./60% RH at 1 month, 2 months, 3 months, 6 months, 12 months, or 24 months.

50. The softgel capsule of any one of the preceding items, wherein the softgel capsule has an assay stability of at least about 90% when tested at 30° C./65% RH at 1 month, 2 months, 3 months, 6 months, 12 months, or 24 months.

51. The softgel capsule of any one of the preceding items, wherein the softgel capsule has an assay stability of at least about 92% when tested at 30° C./65% RH at 1 month, 2 months, 3 months, 6 months, 12 months, or 24 months.

52. The softgel capsule of any one of the preceding items, wherein the softgel capsule has an assay stability of at least about 94% when tested at 30° C./65% RH at 1 month, 2 months, 3 months, 6 months, 12 months, or 24 months.

53. The softgel capsule of any one of the preceding items, wherein the softgel capsule has an assay stability of at least about 96% when tested at 30° C./65% RH at 1 month, 2 months, 3 months, 6 months, 12 months, or 24 months.

54. The softgel capsule of any one of the preceding items, wherein the softgel capsule has an assay stability of at least about 98% when tested at 30° C./65% RH at 1 month, 2 months, 3 months, 6 months, 12 months, or 24 months.

55. The softgel capsule of any one of the preceding items, wherein the softgel capsule has an assay stability of at least about 99% when tested at 30° C./65% RH at 1 month, 2 months, 3 months, 6 months, 12 months, or 24 months.

56. The softgel capsule of any one of the preceding items, wherein the softgel capsule has an assay stability of at least about 90% when tested at 40° C./75% RH at 1 month, 2 months, 3 months, 6 months, 12 months, or 24 months.

57. The softgel capsule of any one of the preceding items, wherein the softgel capsule has an assay stability of at least about 92% when tested at 40° C./75% RH at 1 month, 2 months, 3 months, 6 months, 12 months, or 24 months.

58. The softgel capsule of any one of the preceding items, wherein the softgel capsule has an assay stability of at least about 94% when tested at 40° C./75% RH at 1 month, 2 months, 3 months, 6 months, 12 months, or 24 months.

59. The softgel capsule of any one of the preceding items, wherein the softgel capsule has an assay stability of at least about 96% when tested at 40° C./75% RH at 1 month, 2 months, 3 months, 6 months, 12 months, or 24 months.

60. The softgel capsule of any one of the preceding items, wherein the softgel capsule has an assay stability of at least about 98% when tested at 40° C./75% RH at 1 month, 2 months, 3 months, 6 months, 12 months, or 24 months.

61. The softgel capsule of any one of the preceding items, wherein the softgel capsule has an assay stability of at least about 99% when tested at 40° C./75% RH at 1 month, 2 months, 3 months, 6 months, 12 months, or 24 months.

62. The softgel capsule of any of the preceding items, wherein the softgel capsule remains intact for at least about 15 minutes, at least about 30 minutes, at least about 1 hour, at least about 2 hours, at least about 3 hours, at least about 4 hours, or at least about 5 hours in an acidic medium, wherein a dissolution test is performed in a USP Apparatus II with paddles at a speed of 50 rpm in pH 1.2 medium.

63. The softgel capsule of any one of the preceding items, wherein the softgel capsule remains intact for at least about 15 minutes, at least about 30 minutes, at least about 1 hour, at least about 2 hours, at least about 3 hours, at least about 4 hours, or at least about 5 hours, wherein a disintegration test is performed in a USP Apparatus II with paddles at a speed of 50 rpm in pH 1.2 medium.

64. The softgel capsule any one of the preceding items, wherein the softgel capsule disintegrates in pH 6.8 buffer in about 60 minutes or less, in about 45 minutes or less, in about 30 minutes or less, in about 20 minutes or less, in about 10 minutes or less, or in about 5 minutes or less.

65. The softgel capsule of any of the preceding items, wherein the softgel capsule remains intact for at least about 15 minutes, at least about 30 minutes, at least about 1 hour, at least about 2 hours, at least about 3 hours, at least about 4 hours, or at least about 5 hours in pH 1.2 medium and disintegrate in pH 6.8 buffer in about 60 minutes or less, in about 45 minutes or less, in about 30 minutes or less, in about 20 minutes or less, in about 10 minutes or less, or in about 5 minutes or less.

66. The softgel capsule of any of the preceding items, wherein the total impurity does not exceed about 0.5%, about 0.4%, about 0.3%, about 0.2%, about 0.1% or about 0.01%, wherein the total impurity is measured per current USP Monograph test method.

67. The softgel capsule of any of the preceding items, wherein the total impurity does not exceed about 0.3%.

68. A process for producing the softgel capsule of any one of items 1-67, comprising encapsulating the fill composition in the shell composition to form the softgel capsule and drying the softgel capsule.

69. The process of item 68, wherein prior to encapsulating a gel conversion occurs for the shell composition.

EXAMPLES

Specific embodiments of the invention will now be demonstrated by reference to the following examples. It should be understood that these examples are disclosed solely by way of illustrating the invention and should not be taken in any way to limit the scope of the present invention.

Shell compositions with different enteric polymers were developed. The shell compositions are presented in Tables 1 and 2.

TABLE 1

Shell composition including an amidated pectin

| Ingredients | % |
|---|---|
| Glycerin | 4.0-30.0 |
| Sorbitol Sorbitan Solution | 2.0-35.00 |
| Pectin | 3.0-16 |
| Gellan Gum | 0.2-2.0 |
| Dextrose | 0.01-2.0 |
| Purified Water | 8.0-20.0 |
| Gelatin | 30-48 |
| Total | 100.0 |

TABLE 2

Shell composition including Non-amidated pectin

| Ingredients | % |
|---|---|
| Pigskin Gelatin | 20.0-55.0 |
| Glycerin | 2.0-36.0 |
| Sorbitol Sorbitan Solution | 2.0-40.0 |
| Pectin | 3.0-18.0 |
| Methyl acrylic acid copolymer | 2.0-16.0 |
| Gellan Gum | 0.2-2.5 |
| Dextrose | 0.01-2.0 |
| Purified Water | 8.0-16.0 |
| Total | 100.0 |

The gel conversion of the shell composition is shown in Table 3.

TABLE 3

Ingredients for Gel Conversion.

| Item Description | g/kg of Gel mass |
|---|---|
| Shell Composition | — |
| FD&C Yellow 6 | 0.04-2.4 |
| Titanium Dioxide | 0.3-5.0 |
| Purified Water | 20.0-50.0 |

Two fill compositions were also developed and encapsulated using the shell compositions of Tables 1 and 2. The fill compositions are shown in Tables 4 and 5.

TABLE 4

Fill Composition without Antioxidants

| Ingredients | % |
|---|---|
| Bisacodyl | 1.0-10.0 |
| Soybean oil | 70.0-90.0 |
| Fully Hydrogenated Soybean Oil | 2.0-8.0 |
| Total | 100.0 |

TABLE 5

Fill Composition with Antioxidants

| Ingredients | % |
|---|---|
| Bisacodyl | 1.0-10.0 |
| Soybean oil | 70.0-90.0 |
| Fully Hydrogenated Soybean Oil | 2.0-8.0 |
| Butylated Hydroxytoluene (BHT) | 0.1-1.2 |
| Butylated Hydroxyanisole (BHA) | 0.05-1.4 |
| Total | 100.0 |

Gel masses were prepared using a melter. Colorants were added directly to the melter during gel mass preparation. The fill materials were mixed using a mixing vessel. Two fill batches were prepared and divided up for four (4) finished product sublots/batches. Encapsulation of the four (4) finished product sublots/batches was performed. The theoretical batch size was 5000 softgels for all four batches. The in-process seal thickness check results are summarized in Table 6 below.

TABLE 6

| In-Process Seal thickness | | |
|---|---|---|
| Batch Number | Leading Seal (in) | Trailing Seal (in) |
| 1 | 0.025 | 0.016 |
| 2 | 0.021 | 0.015 |
| 3 | 0.023 | 0.018 |
| 4 | 0.025 | 0.019 |

Drying was carried out using a drying cabinet. After 24 hours, the hardness of all 4 lots capsules reached the drying completion requirement. After the drying was completed, Bisacodyl softgel 5 mg capsules were inspected for defects, and washed using Lecithin/ethanol solution and packaged into sealed plastic bags.

All four finished product batches were packaged into 100 cc HDPE bottles (100 softgels per bottle), induction sealed, and were placed on stability study under various stability conditions, 25° C./60% RH, 30° C./65% RH and 40° C./75% RH, respectively. The four batches are summarized in Table 7.

TABLE 7

| Batch Design Summary | | | |
|---|---|---|---|
| Batch Number | Lot # | Shell Composition | Fill Composition |
| 1 | 20MC-126A | Composition of Table 1 (Amidated Pectin) | Composition of Table 4 (No Antioxidant) |
| 2 | 20MC-128A | Composition of Table 1 (Amidated Pectin) | Composition of Table 5 (With Antioxidant) |
| 3 | 20MC-126B | Composition of Table 2 (Non-Amidated Pectin) | Composition of Table 4 (No Antioxidant) |
| 4 | 20MC-128B | Composition of Table 2 (Non-Amidated Pectin) | Composition of Table 5 (With Antioxidant) |

Two-Stage Dissolution Test

Table 8 summarizes the 2-stage dissolution test results for enteric Bisacodyl 5 mg softgels at T0. Batches 1 and 2 met USP requirement for 1-stage dissolution at T0 time point. Both lots were encapsulated using the gel mass prepared using amidated pectin as described in Table 1. It was found that the capsule made with non-amidated pectin, i.e. Batches 3 and 4, need an extra curing process to enhance gelatin and pectin interaction in order to meet USP dissolution requirement. Batches 3 and 4 also satisfied the USP requirement for two stage-dissolution at T0 time point as well.

TABLE 8

| Two-Stage Dissolution Test Results for T0 Samples | | | | |
|---|---|---|---|---|
| Sample | Conditions | Paddle Speed | Disintegration Results | |
| Batch 1 | T = 0 | 50 RPM | Acid Stage (pH = 1.2) | Intact for 120 min |
| | | | Buffer Stage (pH = 6.8) | 7 min |
| Batch 2 | | | Acid Stage (pH = 1.2) | Intact for 120 min |
| | | | Buffer Stage (pH = 6.8) | 3 min |
| Batch 3 (Cured 10 days @ 40° C.) | | | Acid Stage (pH = 1.2) | Intact for 120 min |
| | | | Buffer Stage (pH = 6.8) | 7 min |
| Batch 4 (Cured 10 days @ 40° C.) | | | Acid Stage (pH = 1.2) | Intact for 120 min |
| | | | Buffer Stage (pH = 6.8) | 4 min |

Test Condition: USP APP II with paddles at 50 RPM and 750 ml 0.1 N HCl medium at 37° C.

The test results of T12 months are presented in Table 9. The two-stage visual dissolution test includes visually inspecting the capsules to see if capsules opened and released any fill in acidic stage or in buffer stage and if they fully released the contents in buffer stage.

TABLE 9

| Two-Stage Visual Dissolution Test Results for T0 Samples | | | | |
|---|---|---|---|---|
| Sample | Conditions | Paddle Speed | Disintegration Results | |
| Batch 1 | T = 0 | 50 RPM | Acid Stage (pH = 1.2) | Intact for 120 min |
| | | | Buffer Stage (pH = 6.8) | 2 min |
| Batch 2 | | | Acid Stage (pH = 1.2) | Intact for 120 min |
| | | | Buffer Stage (pH = 6.8) | 5 min |
| Batch 3 (Cured 10 days @ 40° C.) | | | Acid Stage (pH = 1.2) | Intact for 120 min |
| | | | Buffer Stage (pH = 6.8) | 6 min |
| Batch 4 (Cured 10 days @ 40° C.) | | | Acid Stage (pH = 1.2) | Intact for 120 min |
| | | | Buffer Stage (pH = 6.8) | 4 min |

Test Condition: USP APP II with paddles at 50 RPM and 750 ml 0.1 N HCl medium and pH6.8 phosphate buffer at 37° C.

Disintegration Test

A disintegration test was also conducted on the batches. Table 10 summarizes the disintegration test results for enteric Bisacodyl 5 mg softgels at T0, T1 and T2 stability time points. It was found that Batch 1 met USP requirement for disintegration at T0 and T1, and EP requirement at T2. Batch 2 met the EP requirement for disintegration test at all testing points, T0, T1 and T2. Both batches were encapsulated using the shell composition having amidated pectin. Batches 3 and 4 failed disintegration tests at all stability time points. Without being limited to a theory, the inventors believe that this was due to the use of non-amidated pectin for the shell composition. Additional test results are presented in Tables 11-15.

TABLE 10

| 2-Hour EP Disintegration Test Results for T0, T1 and T2 Samples | | | |
|---|---|---|---|
| Sample | Conditions | Disintegration Result | |
| Batch 1 | T = 0 | Acid Stage (pH = 1.2) | 64 min |
| | | Buffer Stage (pH = 6.8) | NA |
| Batch 2 | | Acid Stage (pH = 1.2) | Intact for 120 min |
| | | Buffer Stage (pH = 6.8) | 9 min |
| Batch 3 | | Acid Stage (pH = 1.2) | 33 min |
| | | Buffer Stage (pH = 6.8) | NA |
| Batch 4 | | Acid Stage (pH = 1.2) | 26 min |
| | | Buffer Stage (pH = 6.8) | NA |
| Batch 1 | T = 1M 40° C./75% RH | Acid Stage (pH = 1.2) | 76 min |
| | | Buffer Stage (pH = 6.8) | NA |

TABLE 10-continued

2-Hour EP Disintegration Test Results for T0, T1 and T2 Samples

| Sample | Conditions | Disintegration Result | |
|---|---|---|---|
| Batch 2 | | Acid Stage (pH = 1.2) | Intact for 120 min |
| | | Buffer Stage (pH = 6.8) | 8 min |
| Batch 1 | T = 2M | Acid Stage (pH = 1.2) | Intact for 120 min |
| | 40° C./75% RH | Buffer Stage (pH = 6.8) | 9 min |
| Batch 2 | | Acid Stage (pH = 1.2) | Intact for 120 min |
| | | Buffer Stage (pH = 6.8) | 10 min |
| Batch 3 | | Acid Stage (pH = 1.2) | 41 min |
| | | Buffer Stage (pH = 6.8) | NA |
| Batch 4 | | Acid Stage (pH = 1.2) | 36 min |
| | | Buffer Stage (pH = 6.8) | NA |
| EP 5.9.2 | Apparatus A; 2-hour Acidic stage (850 ml 0.1N HCl, pH = 1.2; 1-hour Sodium phosphate buffer stage 850 ml, pH = 6.8) | | |

TABLE 11

2-Hour EP Disintegration Test Results for T3 Samples

| Sample | Stability Condition | Disintegration Result | |
|---|---|---|---|
| Batch 1 | 3 Months | Acid Stage (pH = 1.2) | Intact for 120 min |
| | 40° C./75% RH | Buffer Stage (pH = 6.8) | 12 min |
| Batch 2 | | Acid Stage (pH = 1.2) | Intact for 120 min |
| | | Buffer Stage (pH = 6.8) | 9 min |
| Batch 3 | | Acid Stage (pH = 1.2) | 46 min |
| | | Buffer Stage (pH = 6.8) | NA |
| Batch 4 | | Acid Stage (pH = 1.2) | 36 min |
| | | Buffer Stage (pH = 6.8) | NA |
| Batch 1 | 3 Months | Acid Stage (pH = 1.2) | 90 min |
| | 25° C./60% RH | Buffer Stage (pH = 6.8) | NA |
| Batch 2 | | Acid Stage (pH = 1.2) | Intact for 120 min |
| | | Buffer Stage (pH = 6.8) | 10 min |
| Batch 3 | | Acid Stage (pH = 1.2) | 38 min |
| | | Buffer Stage (pH = 6.8) | NA |
| Batch 4 | | Acid Stage (pH = 1.2) | 38 min |
| | | Buffer Stage (pH = 6.8) | NA |
| EP 5.9.2 | Apparatus A; 2-hour Acidic stage (850 ml 0.1N HCl, pH = 1.2; 1-hour Sodium phosphate buffer stage 850 ml, pH = 6.8) | | |

Table 12 summarizes the results of 1-hour USP disintegration tests at T3 time point.

TABLE 12

1-Hour USP Disintegration Test Results for T3 Samples

| Sample | Stability Condition | Disintegration Result | |
|---|---|---|---|
| Batch 1 | 3 Months | Acid Stage (pH = 1.2) | Intact for 60 min |
| | 40° C./75% RH | Buffer Stage (pH = 6.8) | 12 min |
| Batch 2 | 3 Months | Acid Stage (pH = 1.2) | Intact for 60 min |
| | 25° C./60% RH | Buffer Stage (pH = 6.8) | 9 min |

Table 13 summarizes the results of 2-hour EP disintegration tests at T6 stability time point. Batch 1 met EP requirement for disintegration at T6 time point. Batches 2-4 still failed disintegration test at T6 time point.

TABLE 13

2-Hour EP Disintegration Test Results for T6 Samples

| Sample | Stability Condition | Disintegration Result | |
|---|---|---|---|
| Batch 1 | 6 Months | Acid Stage (pH = 1.2) | Intact for 120 min |
| | 40° C./75% RH | Buffer Stage (pH = 6.8) | 16 min |
| Batch 2 | | Acid Stage (pH = 1.2) | Intact for 120 min |
| | | Buffer Stage (pH = 6.8) | 11 min |
| Batch 3 | | Acid Stage (pH = 1.2) | 60 min |
| | | Buffer Stage (pH = 6.8) | NA |

TABLE 13-continued

2-Hour EP Disintegration Test Results for T6 Samples

| Sample | Stability Condition | Disintegration Result | |
|---|---|---|---|
| Batch 4 | | Acid Stage (pH = 1.2) | 79 min |
| | | Buffer Stage (pH = 6.8) | NA |
| 20MC-126A | 6 Months | Acid Stage (pH = 1.2) | 73 min |
| | 25° C./60% RH | Buffer Stage (pH = 6.8) | NA |
| 20MC-128A | | Acid Stage (pH = 1.2) | Intact for 120 min |
| | | Buffer Stage (pH = 6.8) | 10 min |
| 20MC-126B | | Acid Stage (pH = 1.2) | 40 min |
| | | Buffer Stage (pH = 6.8) | NA |
| 20MC-128B | | Acid Stage (pH = 1.2) | 31 min |
| | | Buffer Stage (pH = 6.8) | NA |
| EP 5.9.2 | Apparatus A; 2-hour Acidic stage (850 ml 0.1N HCl, pH = 1.2; 1-hour Sodium phosphate buffer stage 850 ml, pH = 6.8) | | |

Table 14 summarizes the results of 2-hour EP disintegration tests at T12 stability time point. Batch 2 met EP requirement for disintegration at T12 time point. Batches 1, 3 and 4 still failed disintegration test at T12 time point.

TABLE 14

2-Hour EP Disintegration Test Results for T12 Samples

| Sample | Stability Condition | Disintegration Result | |
|---|---|---|---|
| Batch 1 | 12 Months | Acid Stage (pH = 1.2) | 96 min |
| | 30° C./75% RH | Buffer Stage (pH = 6.8) | 22 min |
| Batch 2 | | Acid Stage (pH = 1.2) | Intact for 120 min |
| | | Buffer Stage (pH = 6.8) | 16 min |
| Batch 3 | | Acid Stage (pH = 1.2) | 41 min |
| | | Buffer Stage (pH = 6.8) | 25 min |
| Batch 4 | | Acid Stage (pH = 1.2) | 45 min |
| | | Buffer Stage (pH = 6.8) | 23 min |
| Batch 1 | 12 Months | Acid Stage (pH = 1.2) | Intact for 120 min |
| | 25° C./60% RH | Buffer Stage (pH = 6.8) | 26 min |
| Batch 2 | | Acid Stage (pH = 1.2) | Intact for 120 min |
| | | Buffer Stage (pH = 6.8) | 19 min |
| Batch 3 | | Acid Stage (pH = 1.2) | 45 min |
| | | Buffer Stage (pH = 6.8) | 26 min |
| Batch 4 | | Acid Stage (pH = 1.2) | 45 min |
| | | Buffer Stage (pH = 6.8) | 24 min |
| EP 5.9.2 | Apparatus A; 2-hour Acidic stage (850 ml 0.1N HCl, pH = 1.2; 1-hour Sodium phosphate buffer stage 850 ml, pH = 6.8) | | |

Table 15 summarizes the results of 1-hour USP disintegration tests at T12 stability time point.

TABLE 15

1-Hour USP Disintegration Test Results for T12 Samples

| Sample | Stability Condition | Disintegration Result | |
|---|---|---|---|
| Batch 1 | 12 Months | Acid Stage (pH = 1.2) | Intact for 60 min |
| | 30° C./75% RH | Buffer Stage (pH = 6.8) | 3 min |
| Batch 2 | | Acid Stage (pH = 1.2) | Intact for 60 min |
| | | Buffer Stage (pH = 6.8) | 17 min |
| Batch 3 | | Acid Stage (pH = 1.2) | 42 min |
| | | Buffer Stage (pH = 6.8) | NA |
| Batch 4 | | Acid Stage (pH = 1.2) | 40 min |
| | | Buffer Stage (pH = 6.8) | NA |
| Batch 1 | 12 Months | Acid Stage (pH = 1.2) | Intact for 60 min |
| | 25° C./60% RH | Buffer Stage (pH = 6.8) | 14 min |
| Batch 2 | | Acid Stage (pH = 1.2) | Intact for 60 min |
| | | Buffer Stage (pH = 6.8) | 28 min |
| Batch 3 | | Acid Stage (pH = 1.2) | 4 out of 6 capsules leaked |
| | | Buffer Stage (pH = 6.8) | 4 min |

TABLE 15-continued

1-Hour USP Disintegration Test Results for T12 Samples

| Sample | Stability Condition | Disintegration Result | |
|---|---|---|---|
| Batch 4 | | Acid Stage (pH = 1.2) | 45 min |
| | | Buffer Stage (pH = 6.8) | NA |
| USP<2040> | Apparatus A; 1-hour Acidic stage (850 ml 0.1N HCl, pH = 1.2). Capsules transfer from acidic media to 1-hour Sodium phosphate buffer stage (850 ml, pH = 6.8) | | |

As can be seen in the results above, Batches 1 and 2 met USP requirement for disintegration at T12 time point. Batches 3 and 4 still failed disintegration test at T12 time point. The difference in these batches was the type of pectin used. As noted above, Batches 1 and 2 were prepared using amidated pectin, while Batches 3 and 4 were prepared using non-amidated pectin.

Table 16 summarizes the results of 2-hour EP disintegration tests at T24 stability time point. Both Batches 1 and 2 met EP requirement for disintegration at T24 time point.

TABLE 16

2-Hour EP Disintegration Test Results for T24 Samples

| Sample | Stability Condition | Disintegration Result | |
|---|---|---|---|
| Batch 1 | 24 Months 25° C./60% RH | Acid Stage (pH = 1.2) | Intact for 120 min |
| | | Buffer Stage (pH = 6.8) | 26 min |
| Batch 2 | | Acid Stage (pH = 1.2) | Intact for 120 min |
| | | Buffer Stage (pH = 6.8) | 19 min |
| Batch 3 | | Acid Stage (pH = 1.2) | 45 min |
| | | Buffer Stage (pH = 6.8) | 26 min |
| Batch 4 | | Acid Stage (pH = 1.2) | 45 min |
| | | Buffer Stage (pH = 6.8) | 24 min |
| EP 5.9.2 | Apparatus A; 2-hour Acidic stage (850 ml 0.1N HCl, pH = 1.2; 1-hour Sodium phosphate buffer stage 850 ml, pH = 6.8) | | |

Table 17 summarizes the results of 1-hour USP disintegration tests at T24 stability time point. Both Batches 1 and 2 met USP requirement for disintegration at T24 time point.

TABLE 17

1-Hour USP Disintegration Test Results for T24 Samples

| Sample | Stability Condition | Disintegration Result | |
|---|---|---|---|
| Batch 1 | 24 Months 25° C./60% RH | Acid Stage (pH = 1.2) | Intact for 60 min |
| | | Buffer Stage (pH = 6.8) | 14 min |
| Batch 2 | | Acid Stage (pH = 1.2) | Intact for 60 min |
| | | Buffer Stage (pH = 6.8) | 28 min |
| Batch 3 | | Acid Stage (pH = 1.2) | 4 out of 6 capsules leaked |
| | | Buffer Stage (pH = 6.8) | 4 min |
| Batch 4 | | Acid Stage (pH = 1.2) | 45 min |
| | | Buffer Stage (pH = 6.8) | NA |
| USP<2040> | Apparatus A; 1-hour Acidic stage (850 ml 0.1N HCl, pH = 1.2). Capsules transfer from acidic media to 1-hour Sodium phosphate buffer stage (850 ml, pH = 6.8) | | |

Chemical Stability Test

Stability tests were also conducted of Batches 1 to 4.

Tables 18-21 summarize the chemical stability data for samples at T=0, 6, 12, 18 and 24 month time points under various stability conditions. For the analyses, LOQ=0.05% and LOD=0.03%. Per ICH guidelines, the proposed Individual Unknown Impurity Level Specification is 0.15%; the proposed Total Impurities Level Specification is 2.0%.

TABLE 18

Analytical Testing Results for T = 0, 6, 12, 18 and 24M Stability Time Points for Batch 1 (20MC-126A)

| Lot# | Stability condition | Time Point (month) | RRT 0.42 | (PRI RRT 0.67) Impurity B | (PRI RRT 0.97) Impurity E | (PRI RRT 1.40) | Total % Impurities | % LC (Assay) |
|---|---|---|---|---|---|---|---|---|
| 20MC-126A | Ambient* | 0 | ND | 0.10 | 0.05 | 0.05 | 0.20 | 97.0 |
| | 25° C./60% RH* | 6 | ND | 0.11 | <LOQ | 0.05 | 0.16 | 93.7 |
| | 40° C./75% RH* | | 0.08 | 0.18 | <LOQ | 0.05 | 0.31 | 94.2 |
| | 25° C./60% RH | 12 | ND | 0.06 | <LOQ | <LOQ | 0.06 | 97.9 |
| | 30° C./65% RH | | ND | 0.07 | <LOQ | 0.06 | 0.13 | 94.1 |
| | 25° C./60% RH | 18 | ND | 0.11 | <LOQ | 0.05 | 0.16 | 95.3 |
| | 30° C./65% RH | | ND | 0.11 | <LOQ | <LOQ | 0.11 | 92.4 |
| | 25° C./60% RH | 24 | ND | 0.06 | <LOQ | <LOQ | 0.06 | 97.9 |
| | 30° C./65% RH | | 0.06 | 0.11 | <LOQ | 0.05 | 0.22 | 97.5 |

TABLE 19

Analytical Testing Results for T = 12, 18 and 24M Stability Time Points for Batch 2 (20MC-126B)

| Lot# | Stability condition | Time Point (month) | (PRI RRT 0.67) Impurity B | (PRI RRT 0.97) Impurity E | (PRI RRT 1.40) | Total % Impurities | % LC (Assay) |
|---|---|---|---|---|---|---|---|
| 20MC-126B | 25° C./60% RH | 12 | 0.05 | <LOQ | 0.05 | 0.10 | 87.8 |
| | 30° C./65% RH | | 0.06 | <LOQ | 0.06 | 0.11 | 92.8 |
| | 25° C./60% RH | 18 | 0.13 | 0.07 | 0.05 | 0.25 | 88.6 |
| | 30° C./65% RH | | 0.10 | <LOQ | 0.06 | 0.16 | 89.5 |

TABLE 19-continued

Analytical Testing Results for T = 12, 18 and 24M Stability Time Points for Batch 2 (20MC-126B)

| Lot# | Stability condition | Time Point (month) | (PRI RRT 0.67) Impurity B | (PRI RRT 0.97) Impurity E | (PRI RRT 1.40) | Total % Impurities | % LC (Assay) |
|---|---|---|---|---|---|---|---|
| | 25° C./60% RH | 24 | 0.07 | <LOQ | 0.05 | 0.12 | 96.6 |
| | 30° C./65% RH | | 0.09 | <LOQ | <LOQ | 0.09 | 94.0 |

TABLE 20

Analytical Testing Results for T = 0, 6, 12, 18 and 24M Stability Time Points for Batch 3 (20MC-128A)

| Lot# | Stability condition | Time Point (month) | RRT 0.47 | (PRI RRT 0.67) Impurity B | (PRI RRT 0.97) Impurity E | (PRI RRT 1.40) | RRT 1.46 | Total % Impurities | % LC (Assay) |
|---|---|---|---|---|---|---|---|---|---|
| 20MC-128A | Ambient* | 0 | ND | 0.07 | <LOQ | 0.05 | ND | 0.12 | 95.5 |
| | 25° C./60% RH* | 6 | ND | 0.08 | 0.05 | <LOQ | ND | 0.13 | 95.3 |
| | 40° C./75% RH* | | ND | 0.14 | <LOQ | <LOQ | 0.89 | 1.03 | 95.2 |
| | 25° C./60% RH | 12 | ND | <LOQ | <LOQ | <LOQ | ND | 0.00 | 96.3 |
| | 30° C./65% RH | | ND | 0.06 | <LOQ | <LOQ | ND | 0.06 | 93.7 |
| | 25° C./60% RH | 18 | ND | 0.09 | <LOQ | <LOQ | ND | 0.09 | 93.0 |
| | 30° C./65% RH | | ND | 0.13 | 0.07 | <LOQ | ND | 0.20 | 88.6 |
| | Ambient Bulk | 24 | ND | <LOQ | <LOQ | <LOQ | ND | 0.00 | 97.8 |
| | 25° C./60% RH | | ND | 0.05 | <LOQ | 0.08 | ND | 0.13 | 91.1 |
| | 30° C./65% RH | | 0.08 | 0.07 | <LOQ | 0.05 | ND | 0.20 | 93.7 |

TABLE 21

Analytical Testing Results for T = 12, 18 and 24M Stability Time Points for Batch 4 (20MC-128B)

| Lot# | Stability condition | Time Point (month) | (PRI RRT 0.67) Impurity B | (PRI RRT 0.97) Impurity E | (PRI RRT 1.40) | Total % Impurities | % LC (Assay) |
|---|---|---|---|---|---|---|---|
| 20MC-128B | 25° C./60% RH | 12 | 0.06 | <LOQ | 0.05 | 0.11 | 92.8 |
| | 30° C./65% RH | | 0.06 | <LOQ | <LOQ | 0.06 | 98.7 |
| | 25° C./60% RH | 18 | 0.10 | <LOQ | 0.06 | 0.16 | 92.7 |
| | 30° C./65% RH | | 0.12 | <LOQ | <LOQ | 0.12 | 93.2 |
| | 25° C./60% RH | 24 | 0.06 | <LOQ | 0.06 | 0.12 | 97.6 |
| | 30° C./65% RH | | 0.09 | <LOQ | 0.05 | 0.14 | 97.5 |

Under all stability conditions (40° C./75% RH, 30° C./65% RH, and 25° C./60% RH), all four lots of enteric Bisacodyl 5 mg softgel products with or without antioxidants are chemically stable with slight increase in impurity at 40° C./75% RH as expected.

From these results, an enteric Bisacodyl softgel product was found to be both physically and chemically stable. All batches/lots of Bisacodyl softgel products with or without antioxidants are all chemically stable. The softgel products encapsulated using amidated pectin met either USP disintegration requirement or EP disintegration requirement. The softgel products encapsulated using non-amidated pectin met two stage visual dissolution test requirement.

What is claimed is:

1. A softgel capsule comprising: (a) a fill material comprising bisacodyl or a pharmaceutically acceptable salt, a lipid comprising soybean oil, and a suspending agent comprising hydrogenated vegetable oil; and (b) a shell composition comprising a film forming material, a plasticizer comprising sorbitol and sorbitan, and an enteric polymer comprising pectin;

wherein the fill material comprises about 5 parts by weight to about 10 parts by weight of bisacodyl based on 100 parts by weight of the fill material;

wherein the fill material comprises from about 90 wt % to about 95 wt % of lipid based on a total composition of the fill material;

wherein the softgel capsule remains intact for at least about 15 minutes when a disintegration test is performed in a USP Apparatus II with paddles at a speed of 50 rpm in pH 1.2 medium; and wherein the softgel capsule has an assay stability of at least about 90% when tested at 40° C./75% RH at 1 month.

2. The softgel capsule of claim 1, wherein the film forming material comprises an animal derived polymer or a non-animal derived polymer.

3. The softgel capsule of claim 2, wherein the animal derived polymer comprises gelatin.

4. The softgel capsule of claim 2, wherein non-animal derived polymer comprises gellan gum.

5. The softgel capsule of claim 1, wherein the shell composition further comprises dextrose.

6. The softgel capsule of claim 1, wherein the enteric polymer is methyl acrylic acid copolymer.

7. The softgel capsule of claim 3, wherein the shell composition comprises about 30 wt % to about 80 wt % of a gelatin.

8. The softgel capsule of claim 1, wherein the shell composition comprises about 2 wt % to about 20 wt % of pectin.

9. The softgel capsule of claim 6, wherein the shell composition comprises about 2 wt % to about 16 wt % of methyl acrylic acid copolymer.

10. The softgel capsule of claim 5, wherein the shell composition comprises about 0.01 wt % to about 4 wt % of dextrose.

11. The softgel capsule of claim 3, wherein the gelatin comprises Type A gelatin, Type B gelatin and mixtures thereof.

12. The softgel capsule of claim 1, wherein the shell composition further comprises water.

13. The softgel capsule of claim 1, wherein the fill material further comprises an antioxidant.

14. The softgel capsule of claim 13, wherein the fill material further comprises butylated hydroxytoluene (BHT).

15. The softgel capsule of claims 13, wherein the fill material further comprises butylated hydroxyanisole (BHA).

16. The softgel capsule of claim 13, wherein the fill material comprises about 0.001 parts by weight to about 2 parts by weight of antioxidant based on 100 parts by weight of the fill material.

17. The softgel capsule of claim 14, wherein the fill material comprises about 0.001 parts by weight to about 0.5 parts by weight of BHT based on 100 parts by weight of the fill material.

18. The softgel capsule of claim 15, wherein the fill material comprises about 0.1 parts by weight to about 2 parts by weight of BHA based on a 100 parts by weight of the fill material.

19. The softgel capsule of claim 1, wherein the softgel capsule has an assay stability of at least about 90% when tested at 25° C./60% RH at 1 month.

20. The softgel capsule of claim 1, wherein the softgel capsule has an assay stability of at least about 90% when tested at 30° C./65% RH at 1 month.

21. The softgel capsule of claim 1, wherein the softgel capsule remains intact for at least about 15 minutes in pH 1.2 medium and disintegrate in pH 6.8 buffer in about 60 minutes or less.

22. The softgel capsule of claim 1, wherein the total impurity does not exceed about 0.5%, wherein the total impurity is measured per current USP Monograph test method.

* * * * *